United States Patent
Kirchhof

(10) Patent No.: US 7,682,327 B2
(45) Date of Patent: Mar. 23, 2010

(54) MOBILE HEART-LUNG MACHINE

(75) Inventor: Karsten Kirchhof, Burghaun (DE)

(73) Assignee: Lifebridge Medizintechnik AG, Ampfing (DE)

( * ) Notice: Subject to any disclaimer, the term of this patent is extended or adjusted under 35 U.S.C. 154(b) by 1263 days.

(21) Appl. No.: 10/839,126

(22) Filed: May 6, 2004

(65) Prior Publication Data

US 2005/0004480 A1    Jan. 6, 2005

(30) Foreign Application Priority Data

May 9, 2003    (DE)    ............... 203 07 256

(51) Int. Cl.
 *A61M 37/00*    (2006.01)
 *A61M 1/00*    (2006.01)
(52) U.S. Cl. .................. 604/4.01; 604/6.06; 604/6.1; 604/6.11; 604/6.13; 604/6.16; 604/27; 422/44; 422/45; 422/46
(58) Field of Classification Search ............... 600/6.06, 600/6.1, 6.11, 6.13, 6.16; 422/44, 45, 46
 See application file for complete search history.

(56) References Cited

U.S. PATENT DOCUMENTS

| | | | | |
|---|---|---|---|---|
| 3,890,969 A * | 6/1975 | Fischel | ............... | 604/6.14 |
| 4,610,656 A * | 9/1986 | Mortensen | ............... | 604/6.14 |
| 5,178,603 A * | 1/1993 | Prince | ............... | 604/6.01 |
| 5,308,320 A * | 5/1994 | Safar et al. | ............... | 604/6.14 |
| 5,622,429 A * | 4/1997 | Heinze | ............... | 600/300 |
| 5,814,004 A * | 9/1998 | Tamari | ............... | 604/6.1 |
| 5,820,579 A * | 10/1998 | Plotkin | ............... | 604/5.01 |
| 5,820,593 A * | 10/1998 | Safar et al. | ............... | 604/96.01 |
| 5,879,316 A * | 3/1999 | Safar et al. | ............... | 604/6.01 |
| 5,906,588 A * | 5/1999 | Safar et al. | ............... | 604/64 |
| 5,910,252 A * | 6/1999 | Truitt et al. | ............... | 210/645 |
| 5,980,830 A * | 11/1999 | Savage et al. | ............... | 422/81 |
| 6,071,258 A * | 6/2000 | Dalke et al. | ............... | 604/5.01 |
| 6,126,417 A * | 10/2000 | Roth | ............... | 417/423.7 |
| 6,241,945 B1 * | 6/2001 | Owen | ............... | 422/44 |
| 6,257,265 B1 * | 7/2001 | Brunner et al. | ............... | 137/1 |
| 6,293,773 B1 * | 9/2001 | Doberstein et al. | ............... | 417/420 |
| 6,387,323 B1 * | 5/2002 | Afzal et al. | ............... | 422/45 |
| 6,541,884 B1 * | 4/2003 | Croci | ............... | 310/87 |
| 6,572,821 B2 * | 6/2003 | Knott | ............... | 422/45 |
| 6,733,471 B1 * | 5/2004 | Ericson et al. | ............... | 604/4.01 |
| 7,004,924 B1 * | 2/2006 | Brugger et al. | ............... | 604/6.13 |
| 2003/0220580 A1 * | 11/2003 | Alt | ............... | 600/547 |

(Continued)

FOREIGN PATENT DOCUMENTS

CA    2 361 604    *    8/2001

(Continued)

*Primary Examiner*—Leslie R Deak
*Assistant Examiner*—Adam Marcetich
(74) *Attorney, Agent, or Firm*—Gifford, Krass, Sprinkle, Anderson & Citkowski, P.C.

(57) ABSTRACT

The present invention provides a heart-lung machine which can be carried by one person and can be used independently from an external power supply, consisting of at least three modules (1, 2, 3), wherein a first module (1) contains the blood circulating elements which are necessary for the function of a heart-lung machine, a second module (2) contains a pump drive (9) and an electronic measuring equipment and a control logic (11) and a third module (3) contains the programming unit (14), whereas the second unit is separably connected to the first and the third module.

7 Claims, 1 Drawing Sheet

U.S. PATENT DOCUMENTS

2004/0116819 A1 * 6/2004 Alt .............................. 600/513

FOREIGN PATENT DOCUMENTS

| | | |
|---|---|---|
| DE | 195 36 204 | 1/1997 |
| DE | 29719899 | 1/1998 |
| DE | 199 05 937 | 7/2000 |
| DE | 200 08 961 | 10/2001 |

* cited by examiner

MOBILE HEART-LUNG MACHINE

BACKGROUND OF THE INVENTION

1. Field of the Invention

The invention relates to a mobile heart-lung machine for maintaining the blood circulation.

2. Description of the Prior Art

For maintaining a person's circulation, anoxemic venous blood is removed from the person by means of a heart-lung machine with a cannula and fed to an oxygenator by a blood pump to avoid or eliminate a circulatory arrest or lack of perfusion during an operation as the result of an accident or some other organ failure. In the oxygenator, which performs the function of an artificial lung, the blood is enriched with oxygen and $CO_2$ is removed. Subsequently, the oxygen-rich arterial blood is fed back to the patient's circulation through a cannula after cleaning it in an arterial filter. Heart-lung machines of this type are used for stationary applications in hospitals.

DE 43 43 334 A1 discloses a generic heart-lung machine for mobile use. It has a supporting structure, provided with carrying handles at the front and back, having a bridge-like structure and having standing feet protruding downward. For fixing all component parts of the heart-lung machine, corresponding fastening means are provided. However, in the case of this machine, the functionally important elements are arranged such that they are freely accessible and are consequently not protected against damage, which may impair serviceability during use. In addition, the machine must always be carried by two people.

A mobile heart-lung machine provided with a set of tubes is also disclosed by DE 197 02 098 A1. This machine comprises a loop for feeding blood to an artery, a second loop for removing blood from a vein, a venous reservoir, an oxygenator, a blood pump which is preferably designed as a roller pump, and an oxygen dispenser in the form of an oxygen concentrator connected to the pump on the drive side. Furthermore, the machine has a controller for the oxygen concentrator and the delivery rate of the pump and also connections for a decentralized energy supply and/or for an electrical energy store. Although this heart-lung machine is also intended in particular for mobile use, it cannot normally be handled by one person on account of its size and weight.

Owing to the confined space in an ambulance, it is virtually impossible to take this machine along on an emergency call-out in a ready-to-operate state. The haste required in emergency call-outs, in particular in the case of patients suffering from a failure of the cardiopulmonary function, makes the requirement of setting up the machine prior to use disadvantageous. In addition, after each time they are used, the aforementioned heart-lung machines have to be newly set up and cleaned in a complicated procedure before they are used again. As a result, immediate re-use is not possible.

DE 199 05 937 discloses a heart-lung machine, wherein the elements which circulate the blood on the one hand and the drive and automatic control elements on the other hand are arranged in two separate modules.

It is therefore the object of the present invention to provide a heart-lung machine suitable for mobile use. In particular, it is an object of the present invention to provide a heart-lung machine that can be carried and handled by one person. A further object is that the heart-lung machine is constructed in such a way that the respective elements can easily be exchanged, and thus after use the heart-lung machine can easily and quickly be prepared for the next use.

SUMMARY OF THE INVENTION

The invention relates to a heart-lung machine which can be carried by one person and can be used independently of an external power supply, consisting of at least three modules (1, 2, 3), wherein a first module (1) contains the blood circulating elements which are necessary for the function of a heart-lung machine, a second module (2) contains a pump drive (9) and an electronic measuring equipment and a control logic (11) and a third module (3) contains the programming unit (14), whereas the second unit is separably connected to the first and the third module.

Preferably, the heart-lung machine according to the invention consists of three modules.

In a preferred embodiment of the invention, at least one module of the heart-lung machine is affixed to a housing. In case of a heart-lung machine consisting of three modules, all modules are preferably affixed to a housing.

The present invention furthermore provides a heart-lung machine, wherein the modules can seperably be connected to each other by means of handholds.

Optionally, the housings can seperably be connected to each other by means of handholds.

In another embodiment of the invention, the first module of the mobile heart-lung machine comprises a blood-pump (5), an oxygenator (6), a filter (8) and a blood conveying system.

The first module of the heart-lung-machine may comprise a connection for a venous cannula, a reservoir (4) and a connection for an arterial cannula.

The second module of the heart-lung-machine may comprise a pump drive (9), an electronic measuring equipment and a control logic (11) and valves for adjusting the internal bypass.

The second module of the heart-lung machine preferably comprises an emergency energy supply and operating units for the emergency operation.

The second module of the heart-lung machine may comprise joints to the first and the third module.

Preferably, the second module of the heart-lung machine comprises a storage medium for transferring information from a third module to another third module.

In a preferred embodiment of the invention, the third module of the heart-lung machine comprises an operating surface (13), a computer (14) and a main power supply (15).

In a more preferred embodiment of the invention, the first and the second module of the heart-lung machine can be joined together and can be carried by one person.

Optionally, the first module together with the second module can act as a heart-lung machine without the third module.

Preferably, the connection between the second and the third module of the heart-lung machine is established by a simple current linkage, which compulsory conjoins when assembling the modules or housings.

The invention furthermore provides a module defined above as the first module.

The invention also provides a module defined above as the second module.

The invention also provides a module defined above as the third module.

Finally, the invention provides a heart-lung machine consisting of a first module as defined above and a second module as defined above.

BRIEF DESCRIPTION OF THE DRAWING

A better understanding of the present invention will be had upon reference to the following detailed description when read in conjunction with the drawing in which.

DETAILED DESCRIPTION OF THE INVENTION

Figure 1:
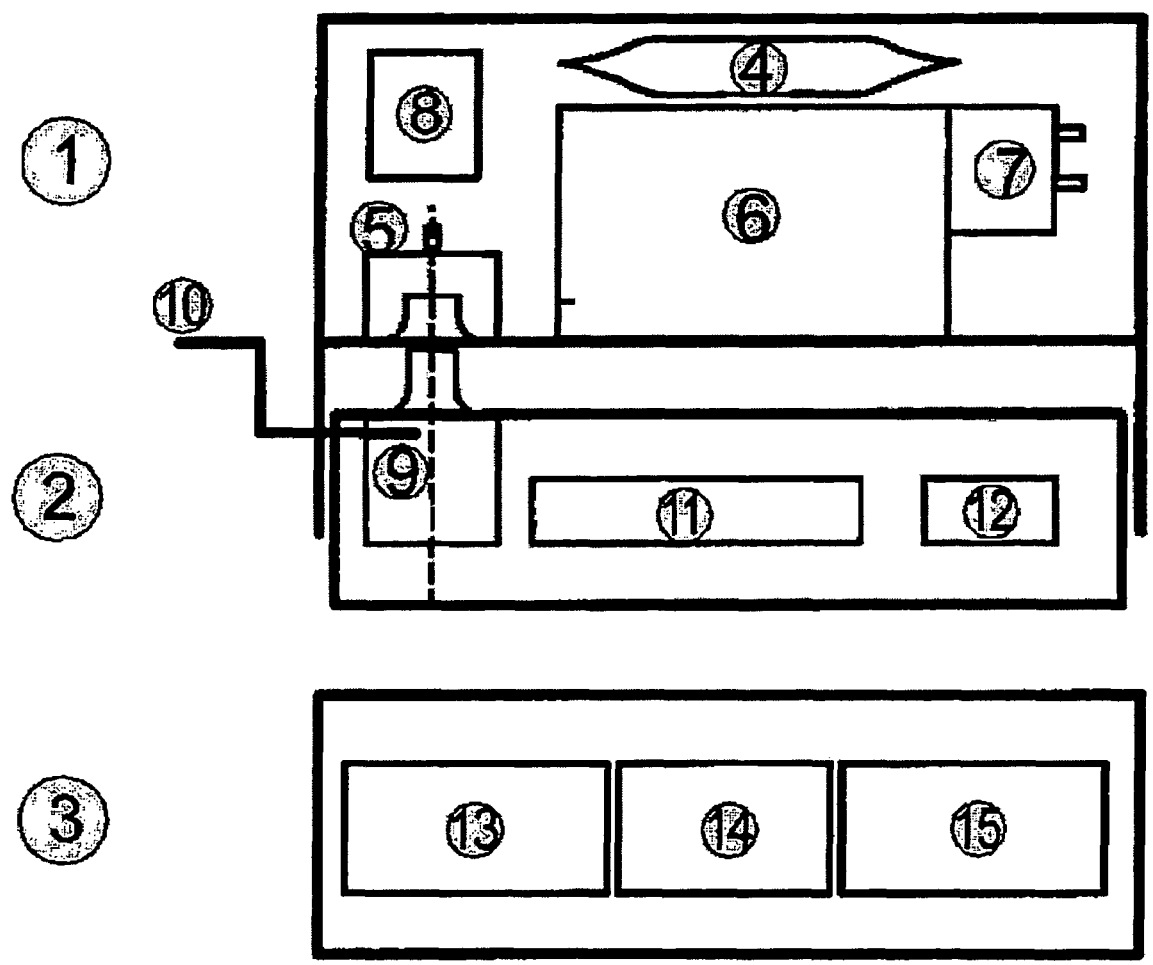
FIG. 1 is a plan diagrammatic view illustrating a preferred embodiment of the present invention.

The modular construction of the heart-lung machine of the invention ensures easy and quick disassembling and reassembling of the heart-lung machine.

Preferably, the heart-lung machine is consists of 3 functional units (modules).

The functional unit wherein the elements coming into contact with blood, such as reservoir (4), pump head (5), oxygenator (6) provided with a heat exchanger (7) or an arterial filter (8), can be embedded is referred to as "patient module" (1).

The functional unit wherein the pump drive (9) provided with a mechanical hand crank (10), the essential sensor part (11) and a backup storage battery (12) can be embedded is referred to as "automatic control module" (2).

The basic unit comprising the operating surface (13) (e.g. touch screen), a computer (14), e.g. a small PC, and a main power supply (15) is referred to as "basic module" (3).

The term "module" as used in the present invention means a unit wherein the respective parts are stably affixed to a support. In the simplest case this support can be a base rack. However, an open or closed housing is preferred. Though the single parts of the unit are stably affixed to the support and/or joined together, the connection can be loosened. The connections are preferable plug-in connections. Preferable all elements are arranged in a housing in order to protect them from mechanical damage. Parts which are not so sensitive may also be arranged outside the housing. The construction of the modules is not limited provided that the single modules per se or a combination of two or three modules can be carried by one person. Therefore, the modules should be compact and must not be constructed in a bulky way. In order to be portable by one person, the size of the heart-lung machine preferably corresponds approximately to the size of an executive case and the weight is preferable not more than 20 kg.

It is the object of the heart-lung machine according to the present invention to maintain and/or replace the cardiopulmonary function. Such a heart-lung machine in general consists of a venous feeding of the patient's blood, a reservoir for balancing the volume, a blood pump for actively supporting the blood-circulation, an oxygenator for enriching the blood with oxygen and for eliminating $CO_2$, a heat exchanger for tempering (heating or cooling of) the blood, an arterial filter provided with a bypass for filtrating the blood, valves for connecting an internal circulation as well as an arterial tube for returning the blood to the patient. The internal bypass is required in order to fill the machine with a blood substitute and to vent the complete system before it is connected to the patient's circulation (priming). The internal volumes should be small in order to keep the volume of the blood substitute as small as possible. Integrating the blood-circulating elements in the housing or moulding them in the plastic housing is also possible to fulfill this feature.

In order to integrate or arrange the very sensitive sensor in or at the respective measuring points, the control module is preferably pre-mounted with the patient module and tested so that the future user receives an element in the form of a plug-in, which then has to be arranged and fixed to the basic module. The plug-in containing the blood-circulating elements like the venous feeding of the patient's blood, reservoir, blood pump, oxygenator, arterial filter provided with a bypass and valves is separated from the control module and disposed after use. The control module is sent back to the manufacturer for recycling. The patient's data saved in the automatic control module and in the basic module can be read out via a data line/port and the data can be made available to the attending hospital for the patient's file or for statistical purposes. By applying the above described operation, an accurate performance of the set up is assured. The "on-site set up" under more difficult conditions as one source of error is essentially limited to the filling and venting of the heart-lung machine.

The necessary software for the drive and automatic control of all processes and operations is preferably contained in a small PC in the basic module. The basic operating data are provided by a basic program. Possible necessary changes can be carried out via the operating surface (e.g. touch screen). These changes can also be saved.

The mobile heart-lung machine is provided with two storage batteries as power supply. The primary energy supply in the basic module is assured by the main storage battery. The control module is provided with a backup storage battery which keeps up the emergency operation over a limited period of time.

A further advantage of the present invention is that after basic setting by the basic module the control module together with the patient's module can also be operated self-sufficiently, that is without the basic module, with an external power supply, e.g. car battery. No further changes or adjustments of the control parameters can be made, however, the number of applications is no longer dependent on the number of the basic modules.

In contrast to other prior art publications like DE 199 05 937 C1, the present invention relates to an heart-lung machine that can easily be carried by one person and consists of various plug-ins provided with the blood-circulating elements, the automatic control elements and sensors for measuring for example the blood temperature, the blood pressure, the oxygen saturation, the volume flow, the internal pressures as well as the basic power supply and software.

With the respective antennas and sensors, inter alia the temperatures at the arterial inlet, the arterial outlet as well as at the oxygenator, the pressure at the venous inlet, at the arterial outlet, between the pump and the oxygenator, the pressure of the $O_2$-supplement, the oxygen saturation at the venous inlet and the arterial outlet, the detection of air bubbles at the venous inlet and the venous outlet as well as the measurement of the blood flow at the arterial outlet are measured.

At the manufacturer's plant the individual modules can be mounted and placed in the housings which protect all elements against external mechanical damage.

The blood guiding in the inside of the patient module is not effected by pre-shaped set of tubes as disclosed by DE 197 02 098 A1, but by a pre-shaped blood guiding system. The advantage of such blood guiding is a lower mechanical strain of the blood, better haemodynamics as well as lower shear rates.

The heart-lung machine which can be carried and operated by one person can be used both directly on-site at an emergency call-out and in a hospital or in a cardiologic practice. A mere in-patient employment in hospitals is also possible.

The connection to the control module is preferably functional, both electrical and mechanical. The electrical connections may connect the automatic control module with the sensor parts for analysis purposes and may afford triggering of the valves. The mechanical connection affords power transmission from the pump drive in the automatic control module to the pump head in the patient module.

In case the automatic control module breaks down, the user has the possibility of keeping up the essential function of the heart-lung machine by manually operating via a hand crank. The automatic control module preferably consists of a housing showing the devices for the complete electronic measurement equipment and automatic control logic, the pump drive, the valves for adjusting the internal bypass, the transitional power supply, the operating unit for the emergency operation, the contacts for the external sensors (temperature, pressure and oxygen saturation, volume flow measurement), the connections to the patient module, the connections to the basic module, the storage medium for transferring information between one basic module and another basic module.

The automatic control module can be arranged in the patient module and is joined with this in the factory. The functional tests and the subsequent calibration are carried out simultaneously. Both modules are supplied to the user as one unit. After use the patient module and automatic control module can be disconnected by the user. The automatic control module can be sent back to the manufacturer in order to be reused after appropriate inspections.

The basic module preferably consists of a housing having a small PC, a LCD-display provided with an operating surface, e.g. touch screen, main power supply, charge devices and connections to the automatic control module.

The purposes of the basic module are to provide the necessary energy, controlling and monitoring the charging, the fault-tolerant and concise operation of the complete system, recording all relevant operation data, documentation of the activities made by the user and the connection to external data processing devices for transferring the recorded information.

The electrical connection between the basic module and automatic control module can be for example a quadripol and serves for transferring energy and information.

The user may keep the basic module, and it can be connected with the unit consisting of automatic control module and patient module by the user before use.

The main advantage over already known heart-lung-machines is that the control module may be returned to the manufacturer again and again which results in a very frequent control of the elements relevant for the control so that software updates can easily be transferred to all applications and the sensitive sensors can be checked, adjusted, revised and calibrated again and again at the plant.

The most complicated operation when mounting the separate system elements is the connection of the patient module with the automatic control module. However, it is now possible that this operation is conducted by the manufacturer, and thus the user is relieved. Above all, in case of an emergency call-out possible sources of error are thus eliminated. As mentioned, before leaving the plant, the patient module and automatic control module together may be tested and calibrated. Thus, the highest accuracy of the measured sensor data are obtained and misoperation by inappropriately joining the quadripolar electrical and mechanical connections between the patient module and automatic control module by the user is excluded.

Since the most complicated connection which brings up the most misoperation can be carried out at the plant, the structure of the heart-lung machine may be simpler and, for example, the machine may be provided with special devices. As a result, the costs for the development and production may be lowered.

Since the connection between the basic module and automatic control module is only necessary for an information and energy transfer, it is possible to use future generations of the heart-lung machine according to the present invention, possibly after a software update of the basic module, together with the existing basic module of the first generation. Therefore, the user's investment in the basic module pays off in the future.

This advantage can be illustrated for example in the case of supplier's problems concerning the delivery of the pump head.

In such a case it would be possible to modify the automatic control module with a suitable adaptation and check it before joining the patient module with a new pump head.

All elements of the automatic control module have to be checked and calibrated at regular intervals. Using this concept, the compliance with these intervals of inspection is not applicable, since the user keeps only the basic module which in general comprises no security relevant elements.

After consultation with the appropriate medical authorities it could be possible to implement a permanent set of emergency programs which, in case of a breakdown of the basic module, may be used with external energy sources (e.g. car battery). These external energy sources are not ideal and detailed operation data cannot be recorded. However, this alternative is to be preferred over a total breakdown of the system.

During disaster operation or multiple crashes it may be desirable to use several heart-lung machine-systems. The number of on-site basic modules limits the number of application cases. With the heart-lung machine according to the present invention it is possible to adjust the system and to effect the priming by the basic module, afterwards to disconnect the basic module from the automatic control module and further use the automatic control module and patient module with an external energy supply. In such a case, the basic module would be available for medicating a further patient. Therefore, only the number of the automatic control module/patient module units would limit the number of patients to be medicated.

LIST OF DESIGNATIONS

1 Patient module
2 Control module
3 Basic module
4 Reservoir
5 Pump head
6 Oxygenator
7 Heat exchanger
8 Arterial filter
9 Pump drive
10 hand crank
11 Electronic measuring equipment and control logic
12 Backup storage battery
13 Touch screen
14 Computer
15 Main power supply

The invention claimed is:

1. A heart-lung machine which can be carried by one person comprising:

a first module which contains blood circulating elements which are necessary for the function of the heart-lung machine, said blood circulating elements including a reservoir, a blood pump and an oxygenator, said blood circulating elements contained in a first unitary housing, a second module physically separable from said first module, said second module containing a pump drive which mechanically drivingly engages said pump only when said first and second modules are connected together, and a control logic, said second module being isolated from blood processed by said blood circulating elements, said pump drive and said control logic contained in a second unitary housing, and a third module physically separable from said first and second module, said third module containing a programming unit, said programming unit including a computer programmed to adjust and prime the blood circulating elements, said programming unit and said computer contained in a third unitary housing, said third module being removable from said first and second module after priming and adjustment of said blood circulating elements whereupon operation of said first and second module continues independently powered by an external power source outside the third module.

2. A heart-lung machine as claimed in claim 1, wherein the second module comprises valves for adjusting an internal bypass.

3. A heart-lung machine as claimed in claim 1, wherein the second module comprises an emergency energy supply and operating units for an emergency operation of the machine.

4. A heart-lung machine as claimed in claim 1, wherein the second module comprises a storage medium for transferring information from the third module to a fourth module.

5. A heart-lung machine as claimed in claim 1, wherein the third module comprises a user interface, a computer and a main power supply.

6. A heart-lung machine as claimed in claim 1, wherein the first and the second module can be joined together and can be carried by one person.

7. A heart-lung machine as claimed in claim 1, wherein a connection between the second and the third module is established by a simple current linkage which compulsory conjoins when assembling the modules.

* * * * *